United States Patent [19]

Burchette, Jr.

[11] Patent Number: 5,057,082
[45] Date of Patent: Oct. 15, 1991

[54] TROCAR ASSEMBLY

[75] Inventor: Robert L. Burchette, Jr., Mayo, S.C.

[73] Assignee: Plastic Injectors, Inc., Spartanburg, S.C.

[21] Appl. No.: 267,497

[22] Filed: Nov. 4, 1988

[51] Int. Cl.$^5$ ............................................. A61M 5/178
[52] U.S. Cl. ...................... 604/164; 604/272; 606/167
[58] Field of Search .................. 604/272–274, 604/164–169, 264; 128/314, 329 R; 606/167, 172, 181, 182, 183–185

[56] References Cited

U.S. PATENT DOCUMENTS

| | | | |
|---|---|---|---|
| 564,581 | 7/1896 | Bakey | 604/274 |
| 737,293 | 8/1903 | Summerfeldt | 604/274 |
| 1,014,128 | 1/1912 | Croue | 604/164 |
| 1,333,745 | 3/1920 | Wescott | 604/272 |
| 2,256,942 | 9/1941 | Duffy | . |
| 2,525,329 | 10/1950 | Wyzenbeek | . |
| 2,878,809 | 3/1959 | Treace | 128/329 R |
| 3,039,468 | 6/1962 | Price | 604/49 |
| 3,090,384 | 5/1963 | Baldwin et al. | 604/272 |
| 3,645,268 | 2/1972 | Capote | . |
| 3,742,958 | 7/1973 | Rundles | . |
| 3,789,852 | 2/1974 | Kim et al. | . |
| 3,994,287 | 11/1976 | Turp et al. | . |
| 4,318,401 | 3/1982 | Zimmerman | . |
| 4,414,974 | 11/1983 | Dotson et al. | 606/167 |
| 4,535,773 | 8/1985 | Yoon | . |
| 4,585,446 | 4/1936 | Kempf | 604/274 |
| 4,601,710 | 7/1986 | Moll | 128/305 |
| 4,610,242 | 9/1986 | Santangelo et al. | . |
| 4,627,838 | 12/1986 | Cross et al. | 604/164 |

FOREIGN PATENT DOCUMENTS 0644253  1/1946  Denmark ............................ 604/272

Primary Examiner—C. Fred Rosenbaum
Assistant Examiner—K. Daley
Attorney, Agent, or Firm—Dority & Manning

[57] ABSTRACT

An obturator is disclosed as being of a throwaway, single use, structure, preferably fully formed of thermoplastic, polymeric material and with a piercing and cutting end defined by non-planar faces having depressions formed therein to present cutting edges. The depressions are shaped by compound curves including a partial spherical surface, and angularly related, generally flat surfaces which define the cutting edges. The surfaces are of a shape and orientation as to provide spatial relief to the edges of the walls of a body to which the obturator is applied, thereby preventing stretching and tearing of the wall.

8 Claims, 3 Drawing Sheets

TROCAR ASSEMBLY

BACKGROUND OF THE INVENTION

The present invention is directed to surgical instruments and, more particularly, to a trocar assembly which may also be useful for endoscopic procedures.

Conventional trocar assemblies utilize trocar obturators or mandrels having pointed tips used to puncture the walls of a body cavity for either draining fluid or for endoscopic procedures. However, the conventional trocar obturator or mandrel is made of stainless steel and utilizes a piercing and cutting end or head tip made from various parts including cutting blades. The obturator or mandrel itself may be relatively complicated, being formed of individual parts joined together by fabrication for the final instrument.

The piercing and cutting surfaces for the conventional trocar mandrel is generally pyramidal in form, and is usually provided with flat side bevels, the surfaces of which converge to define cutting edges. The difficulties and disadvantages of these conventional forms of trocar obturators or mandrels are many. Since these devices are re-used for many surgical procedures, in time, the cutting edges become dulled and nicked from the repeated uses, and perhaps by an occasional inadvertent dropping of an instrument on the floor. Continual use of such devices also increases the risk of initiating and perpetrating the spread of infection to patients who have the misfortune of being subjected to these re-used instruments. In addition, it has also been found that stainless steel has a very high coefficient of friction and has the tendency of dragging or pulling the adjacent walls of a cavity as the instrument is being inserted or removed, thereby causing trauma, undue ripping and/or tearing of tissue around the affected area.

A trocar is disclosed is U.S. Pat. No. 4,654,030 which employs an elongated obturator having a pyramidal shaped piercing head comprising three flatly formed surfaces resulting in a blunt piercing end. These formations of faces will unduly damage the tissue walls surrounding the opening in which the instrument is inserted, by producing ripping and tearing of tissue.

Another conventional embodiment of a trocar obturator is disclosed in U.S. Pat. No. 4,601,710. One of the embodiments is directed to a tubular body having a frustal conical end slotted to receive blades, while in a second embodiment, the piercing tip is formed with three bevels at the end of a cylindrical body portion. By the nature of the disclosed side faces or blades which are blunt and lack suitable curvature for cutting tissue, considerable force is necessary to produce penetration with ensuing damage to the surrounding walls of the tissue. At times, such force may be beyond the capability of the user, and certainly, the application of large amounts of force will be beyond the skill of the operator to apply with precision and efficiency.

Another type of trocar, that for animal use, is disclosed in U.S. Pat. No. 3,039,468. The trocar instrument in this patent utilizes grooves formed in the shank of the trocar device beyond a conical piercing tip. In this arrangement, the conical tip proceeding the grooved sides is too long and would constitute a delay in the use of the grooved portion for penetrating tissues and walls of a cavity. In any event, circular elongated grooves do not lend themselves as efficient types of curves for instruments of this sort which are inserted through tissue and cavity walls for a relatively long distance. Such curves, in fact, add more surface to the instrument thereby increasing the force necessary for the manual insertion and removal of the instrument.

A hyperdermic needle is disclosed in U.S. Pat. No. 3,090,384 which provides a very sharp piercing tip in combination with cutting edges formed of the same material used for the needle. The side surfaces for the cutting faces are flat and may be useful for hyperdermic needles since these instruments have a very small diameter ratio relative to the length of the penetrating piercing tip. Such an arrangement, however, would not be useful for a trocar obturator since the two faces are flat and are not efficient for preventing the dragging and tearing of tissue as the same is inserted into tissue or walls of a cavity.

The principal object of the present invention is to utilize a trocar obturator or mandrel made from inexpensive material and comprising a simple article of manufacture which may be thrown away after a single use.

Another object of the present invention is to utilize a trocar obturator made from material which has a coefficient of friction well below that of stainless steel utilized in conventional obturators and thereby avoid unnecessary damage to tissue during use.

Still another object of the present invention is to minimize the prospect of the initiation and spread of disease or infection made possible with conventional trocar obturators having an assemblage of individual parts which provide spaces wherein contaminants and dirt may become imbedded, and which may not even become fully cleaned, when these instruments are sterilized.

Still another object of the present invention is to utilize a novel design of cutting faces at the piercing end for a trocar obturator which design results in the efficient cutting of tissue around the point of insertion.

In order to avoid the problems and disadvantages of the conventional trocar obturator or mandrels as described above, the present invention was devised so that the obturator or mandrel comprises a single article of manufacture and not the assemblage of individual parts brought together as the finished instrument. The invention also provides that the trocar obturator or mandrel be made of thermoplastic polymeric material which has a coefficient of friction much less than that of stainless steel, or other metals, or metallic plating used in the market today. Furthermore, the invention envisions the use of a more novel arrangement of compound surface formations at the piercing and cutting end of the obturator, the sides being arranged to form cutting edges which, upon movement through the walls of the cavity being worked upon, will ensure that the pierced edges of tissue will slide relatively unimpeded during the cutting stage of the insertion of the obturator so that the tissue does not tear or rip open during this step.

The above recited objects and other advantages will become apparent from the following description taken in conjunction with the drawings wherein:

DESCRIPTION OF A PREFERRED EMBODIMENT

Figure 1:
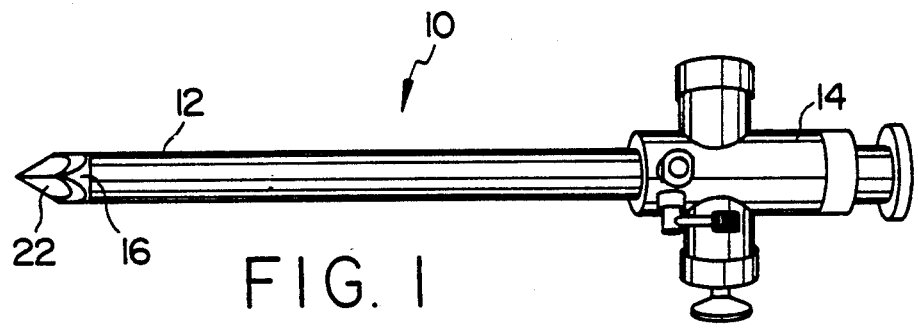
FIG. 1 is an isometric view of a trocar assembly that is illustrative of an embodiment of the invention.

A trocar assembly 10 is illustrated in FIG. 1 as including a trocar tube or cannula 12 having the conventional operating head 14 and a trocar obturator or mandrel 16 releasably supported within the tube. The head 14 may be of conventional fabrication including a valve for the introduction of fluid or gaseous material into the cavity being pierced, or other devices such as viewing eye pieces in the event the trocar assembly is to be utilized as an endoscopic diagnostic instrument.

Figure 2:
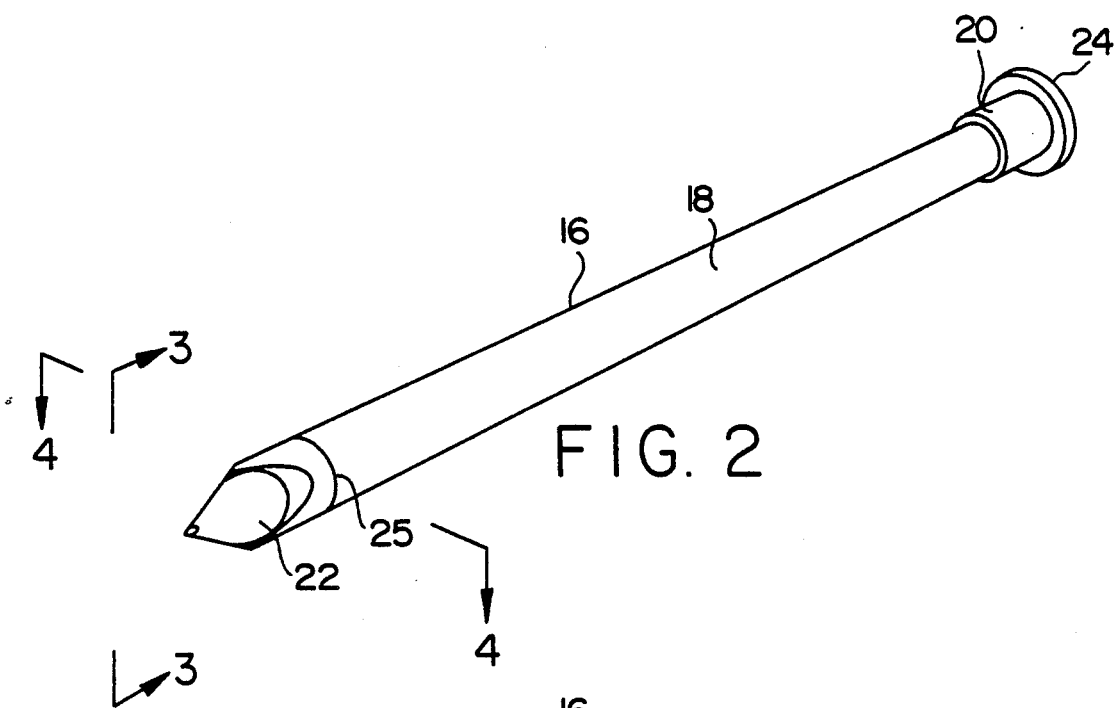
FIG. 2 is an isometric view of the trocar obturator or mandrel of the present invention.

The trocar obturator or mandrel 16 is preferably a unitary, one-piece structure made of polymeric material, either thermoplastic or thermoset and from a process which results in the final manufacture as a single article of manufacture. Examples of suitable polymeric materials include, without limitation, nylons, polyacetals, and polycarbonates. As shown in FIG. 2, the mandrel 16 is formed with a main shank portion 18, a knob-type handle 20 at one end, and at the distal end a piercing and cutting end 22. The knob 20 is made integral with the shank 18 and having an outer surface 24 of suitable shape for the palm of the user. The knob 20 is made of a larger diameter than the shank 18 to permit the insertion of the shank 18 between the user's fingers for easy withdrawal of the obturator. The obturatod may, however, also be produced from separate components and assembled. For example, a stainless steel cutting end having the features as defined herein could be secured to a polymeric shank, or vice versa.

Figure 3:
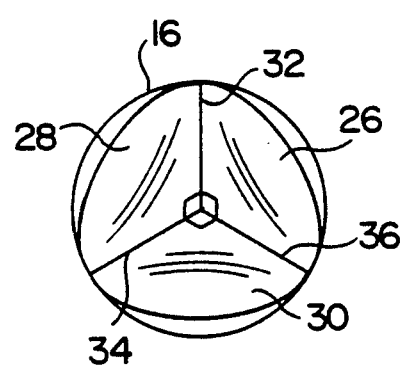
FIG. 3 is an end view of the piercing end of the obturator of FIG. 2.
Figure 4:
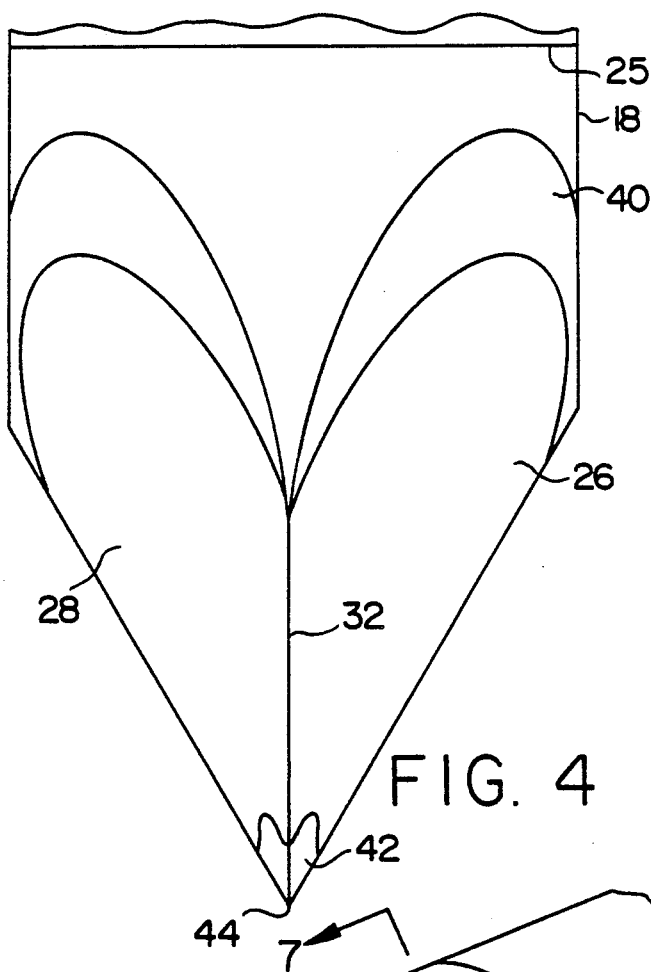
FIG. 4 is an enlarged exploded view of the end portion of the obturator of FIG. 2.
Figure 5:
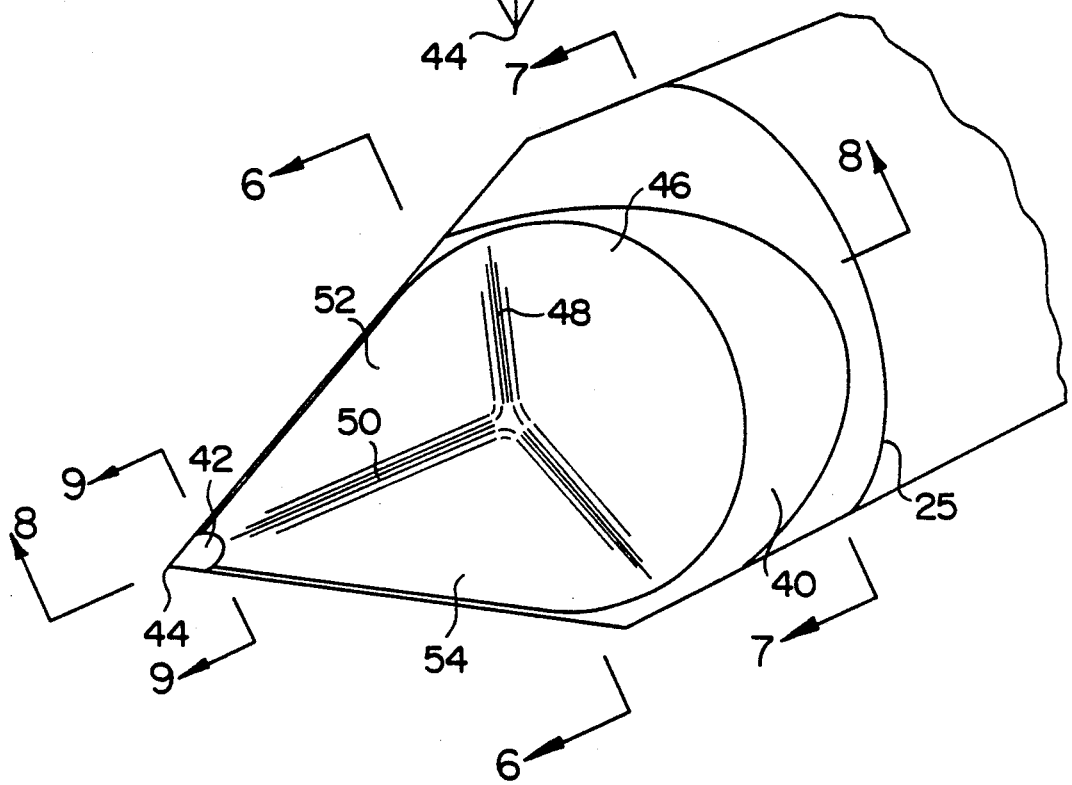
FIG. 5 is an enlarged exploded isometric view of the piercing end.
Figure 6:
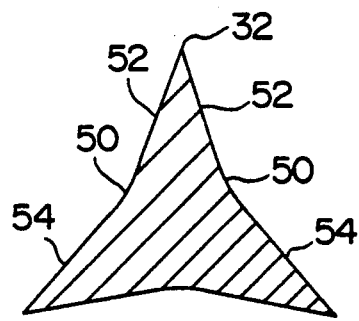
FIGS. 6–9 are cross-sectional views of the piercing and cutting end of the obturator taken along lines 6—6, 7—7, 8—8, 9—9, respectively, in FIG. 5.
Figure 7:
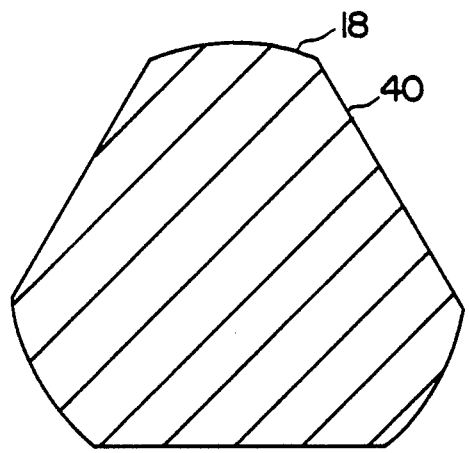
Figure 9:
Figure 8:
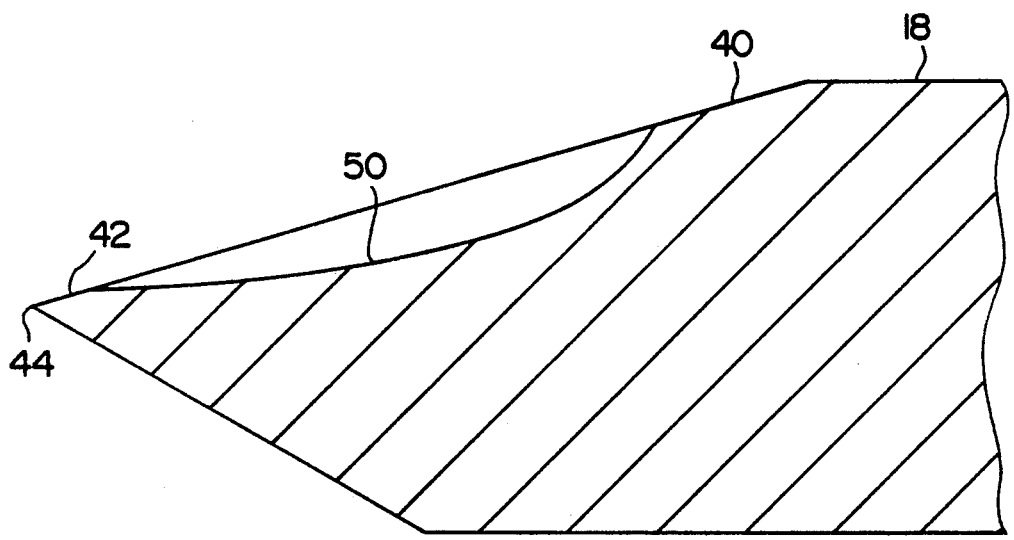

The piercing and cutting end 22 preferably has a diameter slightly larger than that for the shank 18 and provides clearance space within the cannula 12. A tapered shoulder 25 defines the beginning of this space for the shank 18. The obturator end 22 is defined by three faces 26, 28 and 30 of generally concave configuration. As shown in FIG. 3, the adjacent boundary between the face 26 and 28 is formed with a cutting edge 32, the boundary between the faces 28 and 30 by a cutting edge 34 and the boundary between the face 30 and 26 with a cutting edge 36. There could, however, be a common diameter between the largest diameter portion of end 22 and shank 18.

The faces 26, 28, 30 have the identical shape, being irregularly concave in form, that is, being devised with recessed surfaces comprising different curves along planes normal to each other. Since the surfaces are similar, only one, face 26 will be described in detail.

The face 26 at one end, is formed with a flat surface 40 merging with the adjacent cylindrical surface of the shank 18, and at the other end, is formed with a flat surface 42, coplanar with the surface 40, and which defines a piercing tip 44 for the end 22. A surface 46 of generally spherical configuration joins the surface 40 to form a circular boundary line 48, the deepest area in the face 26 is in the form of a groove-like surface 50 which runs along the longitudinal axis of the face beginning near from the surface 42 and merging in the surface 46.

The grooved surface 50 separates two generally flat surfaces 52, 54 which extend angularly upwardly to form the cutting edges 32, 36.

During movement of the piercing end 22 through the walls of a cavity such as an abdominal wall, the tissue or layers of tissue are cut by the edges 32, 34, 36. As this movement continues and the tissues are penetrated by the tip 44 and then cut, the edges of the opening formed thereby will slide along the angularly spaced flat surfaces 52, 54 for each of the faces 26, 28, 30, and thence along the spherical surface 46. During this motion, the walls of the opening do not experience undue forces as the end 22 continues its movement. The shapes, the combination and the orientation of the surfaces 40, 46, 50, 52, 54 are such as to provide continuing and increasing space for the edges of tissue to occupy, thereby offering appropriate relief to the tissue, as the resulting opening in the walls of a cavity becomes larger due to the increasing diameter of the end 22. During this process, there is no stretching of the penetrated and cut edges of the tissue throughout the entire movement of the end 22 until the adjacent end of the shank portion 18 is reached. At this point, the opening in the wall of the cavity is such that no further cutting of tissue is produced and therefore there is no likelihood of undue ripping or tearing of tissue.

Throughout the entire movement of the piercing and cutting end 22 through the walls of the body, the edges of the pierced and cut walls experience very little trauma, ripping or tearing because of the characteristics of the polymeric material of end 22. The frictional characteristics of the polymeric material in combination with the cutting edges of end 22, in fact, enable the obturator to be fully inserted in the walls of a cavity at approximately one-half of the force that is normally required for insertion of the conventional obturator made from stainless steel.

While the foregoing description referred to the use of the invention for piercing and cutting through abdominal walls, it will be understood that the present invention has uses for other cavities in the body and for other parts of the anatomy. For example, the trocar obturator devised in accordance with the present invention may be used in arthroscopy and thorascopy procedures.

While in the foregoing only embodiment of the invention has been disclosed in considerable detail, it will be understood that this was only for illustration purposes and that modifications of the above mode of carrying out the invention which are obvious to those of skill in the art of surgical instrument design, or related fields are intended to be within the scope of the following claims.

What is claimed is:

1. An improved trocar obturator for insertion through body wall portions of humans and animals, comprising:

an elongated shank;

a solid cutting portion permanently secured to one end of said shank and having a plurality of faces each of said faces having a planar surface adjacent an outer free, distal end of same and a planar surface adjacent a proximal end of same, and defining a depression therebetween extending along said face, said faces merging into a cylindrical shank portion at said proximal end of same;

a piercing tip defined by said faces;

straight cutting edges defined at the intersection of each two adjacent faces, said cutting edge converging at said piercing tip and extending rearwardly from said tip towards said shank, said piercing tip and said cutting edges defining a cutting end of said trocar which minimizes tearing of surrounding body tissue during trocar penetration thereof; and knob means located at an end of said shank opposite said cutting end to facilitate use of said trocar.

2. A trocar obturator recited in claim 1 wherein said obturator is disposable.

3. A trocar obturator recited in claim 1 wherein said obturator is of unitary construction.

4. A trocar as defined in claim 1 wherein said shank is polymeric and said cutting portion is metallic.

5. A trocar as defined in claim 1 wherein said shank has a common diameter along at least a portion of the length of same.

6. In a trocar assembly including an elongated hollow trocar tube and an obturator removably supported therein and coaxial with its longitudinal axis, the assembly being adapted for insertion through walls of human or animal bodies, wherein the improvement is an obturator comprising an elongated, solid polymeric shank, said shank having enlarged knob means secured thereto at a proximal end of same and a piercing, solid cutting end secured to a distal end of same, said cutting end having a plurality of faces that intersect to define cutting edges, with said face and said cutting edges inwardly tapering from adjacent said shank forwardly to a point which defines a piercing tip, each of said faces having spaced apart planar surfaces with a depressed area therebetween and extending longitudinally with respect thereto.

7. A trocar assembly as defined in claim 6 wherein the cutting end is polymeric and is of unitary construction with said shank.

8. A trocar assembly as defined in claim 6 wherein said cutting end is metal and is permanently secured to said shank.

* * * * *